United States Patent [19]

Fleer

[11] 4,007,529

[45] Feb. 15, 1977

[54] MOTOR-DRIVEN DENTAL HANDPIECE

[75] Inventor: Ernst Otto Fleer, Bensheim-Auerbach, Germany

[73] Assignee: Siemens Aktiengesellschaft, Berlin & Munich, Germany

[22] Filed: June 24, 1975

[21] Appl. No.: 589,923

[30] Foreign Application Priority Data

July 1, 1974 Germany .......................... 2431472

[52] U.S. Cl. .................................................. 32/27
[51] Int. Cl.² ........................................ A61C 1/10
[58] Field of Search ............... 251/345, 343; 32/26, 32/27

[56] References Cited

UNITED STATES PATENTS 3,425,124   2/1969   Hoffmeister ........................... 32/28

FOREIGN PATENTS OR APPLICATIONS 1,096,337   12/1967   United Kingdom ............... 251/343

*Primary Examiner*—Robert Peshock
*Attorney, Agent, or Firm*—Hill, Gross, Simpson, Van Santen, Steadman, Chiara & Simpson

[57] ABSTRACT

A dental handpiece which includes a driving motor located within an essentially cylindrical housing; energy means infeed conduits for the motor and a supply hose containing at least one cooling medium infeed conduit being connectable to one end of the housing through the intermediary of a connector part, and also containing an energy supply conduit for the motor; and to whose other end there is attachable a gripping member onto a drive shaft extending out of the housing, so as to be readily exchangeable, the gripping member being rotatable with respect to the housing, containing a head portion with a work tool at the free end thereof, and at least one conduit for conveying the cooling medium from the connecting portion for the supply hose to the head portion of the gripping member. The cooling medium conduit is divided along the motor housing and the gripping member into two fixedly displaced conduit portions which are interconnectable between the housing and the gripping member by means of coupling means located concentrically with the drive shaft, a power-transmission shaft engaging with the latter.

13 Claims, 10 Drawing Figures

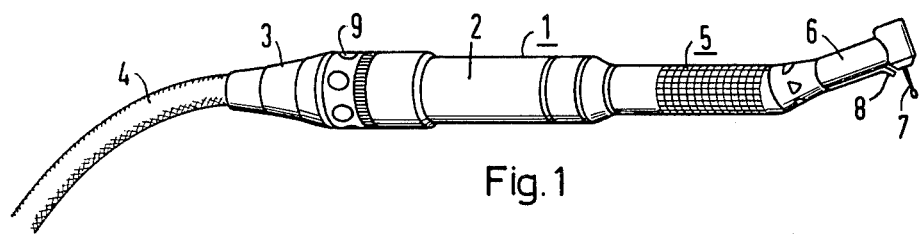
Fig. 1
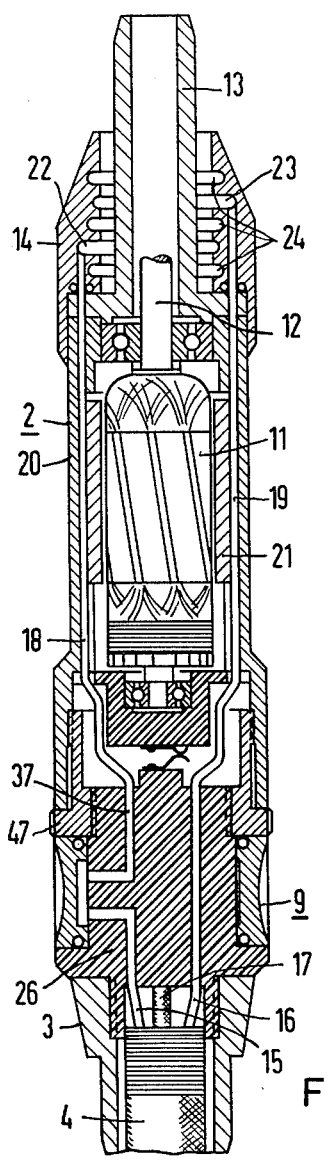
Fig. 2
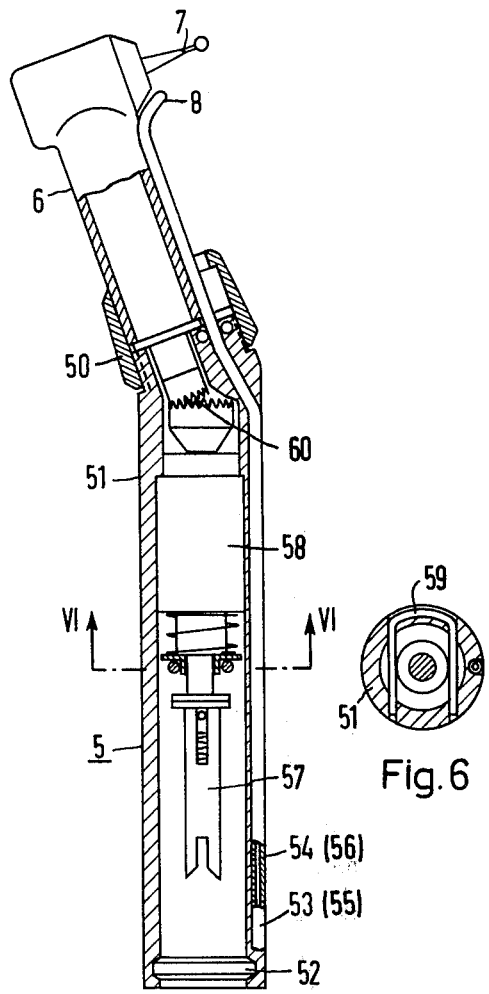
Fig. 5
Fig. 6

MOTOR-DRIVEN DENTAL HANDPIECE

FIELD OF THE INVENTION

The present invention relates to a dental handpiece which includes an electrical motor located within an essentially cyclindrical housing; energy means infeed conduits for the motor and a supply hose containing at least one cooling medium infeed conduit being connectable to one end of the housing through the intermediary of a connector part, and also containing an energy supply conduit for the motor; and to whose other end there is attachable a gripping member onto a drive shaft extending out of the housing, so as to be readily exchangeable, the gripping member being rotatable with respect to the housing, containing a head portion with a work tool at the free end thereof, and at least one conduit for conveying the cooling medium from the connecting portion for the supply hose to the head portion of the gripping member.

DISCUSSION OF THE PRIOR ART

In a dental handpiece of this type, the cooling medium conduit leading to the head portion of the gripping element for purposes of producing a spray at the operative work tool is constructed as a flexible hose conduit, which is located so as to be freely movable from the connector part of the supply hose up to the head portion of the gripping member. However, this arrangement is subject to definite disadvantages. Thus, during the routine exchange of the gripping member, in addition to the mechanical coupling of the handpiece parts, the previously mentioned cooling medium conduit must be pulled off from the connector part, and must be newly pulled onto the other handpiece part. A further disadvantage lies in that the rotatability of the handpiece is limited relative to the motor housing due to the length of the cooling medium hose, with the cooling medium hose not being constructed to be so long, however, as not to further influence the operation of the handpiece, which anyway disturbs during sensitive drilling due to the externally located cooling medium hose. An additional disadvantage encountered lies in that upon the withdrawing or redepositing of the handpiece out of or, respectively, into its associated support or depository, the externally located cooling medium hose which, due to the rotatability of the handpiece, sufficient to some degree, necessarily requires an excess length, may easily become caught or entangled on adjacent handpieces.

SUMMARY OF THE INVENTION

Accordingly, it is an object of the present invention to provide a dental handpiece of the above-mentioned type, which avoids or ameliorates the advantages encountered in the prior art constructions. For this purpose, the present invention provides for in that the cooling medium conduit which leads to the head portion of the gripping member does not exert any disruptive effects on the manipulation of the handpiece, in which the rotatability of the gripping member is not limited with regard to the motor housing, and which affords practially no operative complexities during the handgrip exchange.

The foregoing object is inventively achieved in that the cooling medium conduit is essentially divided along the motor housing and the gripping member into two fixedly displaced conduit portions, which are connectable to each other between the motor housing and gripping member by means of coupling means located concentrically with the drive shaft. By "fixedly displaced" there is meant that the conduits are not located so as to be freely movable, but are fastened to the respective handpiece parts. The conduits themselves need not necessarily be inflexibly constructed, rather it is more readily thinkable that there may be employed flexible plastic material tubes, and that these are arranged in the motor housing or, respectively, the gripping member in the subsequently hereinbelow described manner.

When the gripping member is adapted to be locked with the motor housing, respectively, the drive shaft, by means of a mechanical coupling element, it is advantageous that the coupling means for the transmission of the cooling media be incorporated into the particular attachment member in which there is located the coupling member.

BRIEF DESCRIPTION OF THE DRAWINGS

Further advantageous embodiments and constructions of the invention may now be ascertained from the following detailed description of exemplary embodiments of a dental handpiece, taken in conjunction with the accompanying drawings, in which:

FIG. 1 is a perspective assembly of a dental handpiece shown equipped with a gripping member and thereto attached supply hose;

FIG. 2 is an enlarged longitudinal sectional view of the motor housing of the handpiece;

FIG. 5 is a longitudinal sectional view of the gripping member associated with the motor housing of FIG. 2;

FIG. 6 is a transverse section taken along line VI—VI in FIG. 5;

DETAILED DESCRIPTION

Figure 3:
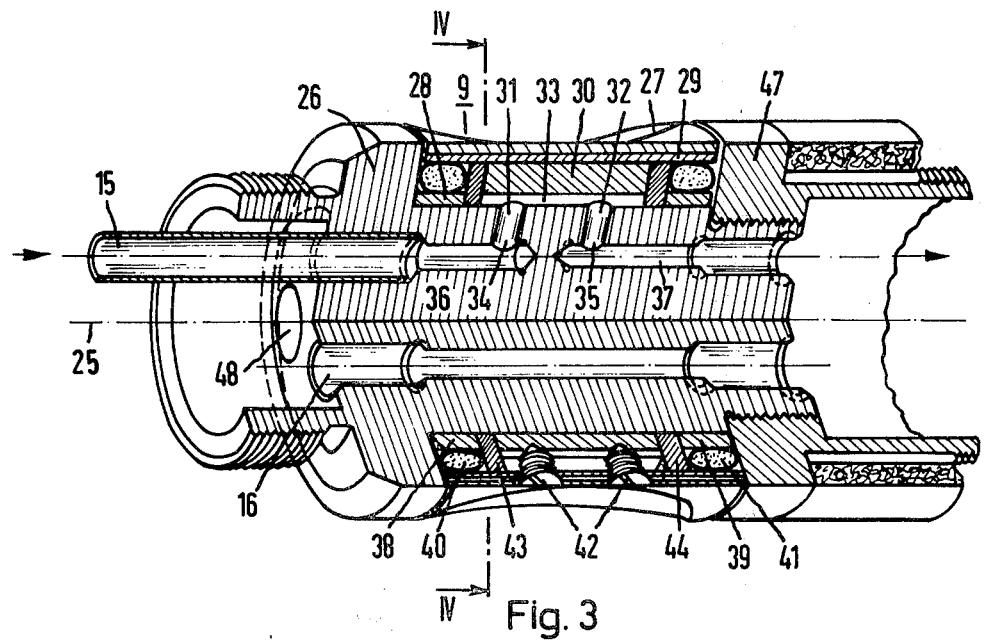
FIG. 3 illustrates a longitudinal section of a flow regulating valve which is associated with the handpiece.

Referring now in detail to the drawings, FIG. 1 perspectively illustrates a dental handpiece 1 including an essentially cylindrical housing 2, one end of the latter having a supply hose 4 connected thereto, by means of a connector part 3, and a grip or gripping member 5 connected to the other end thereof. The gripping member 5 contains a head portion 6 with a work tool 7 (drill). The gripping member 5 is mounted so as to be rotatable relative to the housing and can be secured against axial displacement in the attached position thereof by means of a suitable mechanical coupling element (not shown). At the head portion 6 there projects the end 8 of a cooling medium conduit, described in greater detail hereinbelow, for the supply of a water-air mixture (spray) to the work tool 7, by means of which the location of treatment may be cooled during drilling or grinding. Identified by reference numeral 9 is a valve which is located between the connector part 3 and the motor housing 2, and by means of which there may be provided control over the rate of flow of the cooling medium which is conveyed to the head portion 6 of the handpiece.

FIG. 2 illustrates the housing 2 in a longitudinal sectional view. The housing contains an electric motor 11 having a drive shaft 12, extending towards the gripping member 5, and encompassed by a sleeve 13 which is fastened on the housing by means of an attachment member 14. The latter also contains the above-mentioned coupling element, by means of which the gripping member 5, after the mounting thereof onto the sleeve 13, is locked, in a known manner, against inadvertent axial pull-out or extension.

At the hose-connected end of the housing, in essence, between the connector part 3 and the motor housing 2, there is located the valve 9. Details of this valve are set forth in FIGS. 3 and 4 of the drawings. The supply hose 4 contains an infeed or supply conduit 15 for water, a supply conduit 16 for air, and a conduit passageway for supply of electrical conduits 17 for powering the motor 11. The extensions of the two cooling medium conduits 15, 16 in the region of the motor housing 2 are designated by reference numerals 18 and 19. These cooling medium conduit sections 18, 19 are fixedly displaced within the housing 2, namely between the housing jacket 20 and the stator portions 21 of the motor 11, and terminates in annular passageways 22, 23 in the attachment member 14 which are sealed off with respect to each other by means of sealing rings 24 when the gripping member 5 is mounted on the motor housing. Inasmuch as the conduits 18 and 19, due to technological manufacturing and assembling reasons, cannot be constituted of a single piece, naturally located at the transition locations, for example, between the attachment member 14 and the motor housing 2, or between valve 9 and motor housing 2, are still further sealing elements, whose detailed description and illustration need not be described within the frame of the present disclosure. The two annular passageways or spaces 22 and 23 represent the one portion of the coupling means which provides an operative connection of the cooling media conduits 18, 19 from the motor housing 2 to the gripping member 5. For the sake of simplicity, the cooling medium conduit section is so illustrated whereby the two conduits 18, 19 are offset by 180° with respect to each other. Such an arrangement is however not absolutely necessary. Thus, within the scope of the invention, it is also possible that the two conduits 18 and 19 may extend along the handpiece, immediately adjacent each other, and that the motor housing 2 be located eccentrically with reference to the gripping member 5. The external diameter of the handpiece thereby becomes smaller by the extent of the diameters of the conduits.

FIG. 3 illustrates details of the valve 9. The valve 9 which is connected, on the one hand, to the connector part 3 of FIG. 2 by means of suitable threaded connectors (not described in detail) and, on the other hand, to the one end of the housing jacket 20, essentially consists of a rotationally symmetrical base member 26 which forms the valve body, and whose axis 25 coincides with the longitudinal axis of the handpiece 1. The base member 26 is provided with an annular groove 28 in which there is located the complete closure body of the valve. Viewed from externally towards the interior of the valve, there are provided an actuating ring 27 having gripping recesses, an intermediate ring 29 and the actual closure member 30. The closure member 30 is constituted of a sleeve encompassing the base member 26, and is supported so as to be eccentrically rotatable relative to the axis 25 of the base member. Provided in the cylindrical jacket or sleeve surface 33 of the annular groove 28 are openings 31, 32 of a valve inlet connection 34 and of a valve outlet connector 35 which open radially outwardly from the base member 26. The valve inlet connector 34 communicates with the water supply passageway 15, and the valve outlet connector 35 with the conduit passageway 18 which is offset in the area of the motor housing 2, through intermediary of the conduit section 37. The base member 26 consists of a rotating or spray part in which the passageways are built in, as illustrated, by means of bores or drill holes. At both ends of the annular groove 28 are respectively located plastic material bushings 38, 39 on which there are tension-mounted the resiliently elastic O-rings 40, 41. Two adjusting screws 42 constitute means through which the closure member 30 is pressed against the base member 26.

Two spacer discs are designated by reference numerals 43 and 44, by means of which the actuating ring 27 and the intermediate ring 29 are supported against the base member 26. From the illustration it becomes ascertainable that the two connectors 34 and 35 are located behind each other in the axial plane of the base member 26, and that the actuating ring 27, or respectively, the closure member 30, are so wide whereby the inner wall of the closure member 30, in the closed position of the valve, covers the two openings 31, 32 of the connectors 34 and 35.

Figure 4:
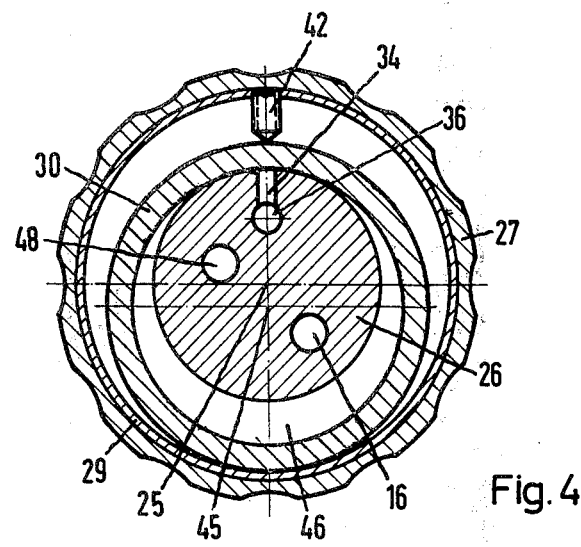
FIG. 4 is a sectional view taken along line IV-IV in FIG. 3.

FIG. 4 illustrates the valve 9 in transverse section taken along line IV-IV in FIG. 3 and, namely, in a closed position. With reference numeral 45 there is designated the symmetrical axis of the closure member 30, extending eccentrically to the symmetric rotational axis 25. The closure member 30 has an internal diameter which is approximately 2/10 mm larger than the external diameter of the base member 26. From the illustration, shown in connection with FIG. 3, it is ascertainable that between the base member 26 and the closure member 30 there is formed a sickle-shaped gap 46 which constitutes the valve chamber. When the actuating ring 27 is rotated, then the closure member 30 is also taken along therewith through the aid of two screws 42. Thereby the gap will increase over the two openings 31 and 32 (FIG. 3), and as a result also the free flow section through the valve. The path of the flowing medium extends in the illustrated direction of the arrow from the supply passageway 15 through the valve inlet connector 34 into the valve chamber 46, and from there finally through the valve outlet connector 35 into the outlet passageway 37 which is connected with the cooling medium conduit 18 (FIG. 2) and which finally communicates with the annular passageway 22 and from there, as may be ascertained from the subsequent FIG. 5, leads to the head portion 5 of the handpiece 1. The compressive force with which the closure member 30 is pressed against the cylindrical jacket surface of the base member 26 may be varied by means of the two adjusting screws 42. For effecting the adjustment of the compressive force, the flanged ring 27 is screwed off from its position on the valve member 26, and the external actuating ring 27 which is provided with the gripping recesses is then pulled off. Designated by reference numeral 48 is a passageway for the conductance of the electrical conduits 17 to the electrical motor 11.

FIG. 5 illustrates the gripping member 5 which is attachable onto the motor housing 2 as shown in FIG. 2. The head portion 6 is screwed onto the cylindrical housing 2 shown in FIG. 2. The head portion 6 is screwed onto the cylindrical housing part 51 by means of a threaded nut 50. An annular groove is designated by reference numeral 52 into which there may engage the previously mentioned coupling element not shown in the Figure (for example, a locking projection for effectuating the mechanical coupling of the two parts 2 and 5. The gripping member 5 is slid onto the sleeve 13 (FIG. 2) until it stops. In this position, the above-mentioned coupling element locks into the annular groove 52 of the gripping member 5. Identified by reference numeral 53 is a recess in the housing part 51, and which is connected with a cooling medium conduit 54 fixedly positioned within the housing part 51. When the handpiece 5 is mounted on the motor housing 2, the recess 53 is in communication with the annular passageway 22. Designated by reference numeral 55 is a further recess extending to the annular passageway 23, the latter of which communicates with a further conduit portion 56 (not shown), which suitably runs in parallel with the conduit 54. The recesses 53 and 55 and the annular passageways 22 and 23 presently form the coupling means for the two cooling medium conduit sections from the motor housing 2 and gripping member 5. Both cooling media conduits 54 and 56 are separately conveyed to the head portion up to the outlet location 8. The air emanating from one conduit and the water emanating from the other conduit there form at the outlet location, respectively, at the drill 7, an air-water mixture (spray). The two annular passageways 22, 23 allow the gripping member 5 to be rotated by more than 360°, in effect practically endlessly, without the conduit path of conveyance being interrupted. It is also to be noted that it is within the scope of the invention that the coupling parts be so arranged whereby annular grooves towards the side of the motor are located internally and the receiving or transition passageway towards the side of the handgrip are located externally; the annular grooves may be arranged in the gripping member and the recesses in the attachment part for the motor housing.

Designated by reference numeral 57 is a shaft which comes into engagement with the drive shaft 12 of the motor 11, as shown in FIG. 2, when the gripping member 5 has been slid onto the sleeve 13 (FIG. 2). The shaft 57 runs in a bearing 58 which is secured against rotation in the housing 51 of the gripping member 5 and against falling out means of a hairpin-like clamp 59. Designated by reference numeral 60 is an end-toothed spur gear drive for transmission of the rotational movement to the work tool 7 which is supported in the head portion.

Figure 8:
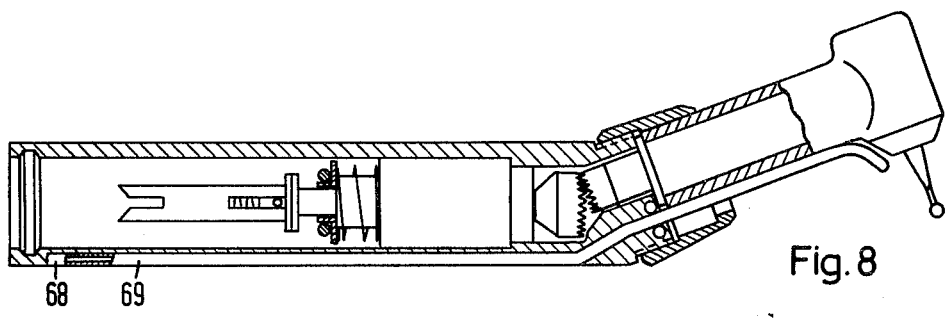
FIG. 8 is a longitudinal sectional view of the gripping member which is associated with the exemplary embodiment pursuant to FIG. 7.
Figure 7:
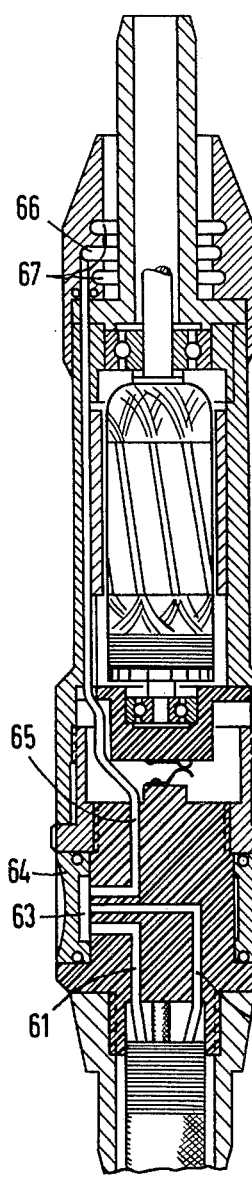
FIG. 7 is a longitudinal sectional view of another embodiment of a cooling medium conduit line located in the motor housing.

FIGS. 7 and 8 illustrate another embodiment of a cooling medium conduit conveyance through the motor housing or, respectively, through the gripping member. Inasmuch as the construction of the motor housing and the gripping member up to the conduit conveyance is fully identical with that of the embodiment of FIGS. 2 and 5, in FIGS. 7 and 8 only the few elements which deviate from the embodiment of FIGS. 2 and 5 are provided with reference numerals.

The water conduit 61 and the air conduit 62 herein terminate in a common mixing passageway of a mixing valve 64. The mixing valve 64, up to the flow path of the conduit 62 (corresponding to element 16 in FIG. 3) is fully identical to the valve 9 which is illustrated in FIG. 3. The air conduit 62 herein extends radially into the mixing passageway 63, the latter of which corresponds to the valve chamber 46 in FIG. 4. It may also be suitable that the conduit 62 extend radially into the inlet passageway 61 (corresponding to element 34 in FIG. 3) and from there into the mixing chamber. Provided at the outlet side of the valve 64 is only a single common conduit 65 for the water-air mixture (spray) which is admixed in the mixing chamber 63. The conduit 65 herein, analogous to the conduits 18 and 19 in FIG. 2, is fixedly offset in the housing of motor handpiece and terminates in an annular passageway 66 which, for the mounted gripping member, is sealed off from ambient air through O-rings 67.

The gripping member which is associated with the motor housing pursuant to FIG. 7 is illustrated in FIG. 8. The foregoing essentially corresponds to the embodiment shown in FIG. 5. However, in this instance, the cooling medium conduit sections consists of a single common conduit for both the air and water media. With the mounting of the gripping member onto the motor housing there is also, in this case, produced an automatic connection between the two cooling media conduit sections (conduit 65 with conduit 69).

Figure 9:
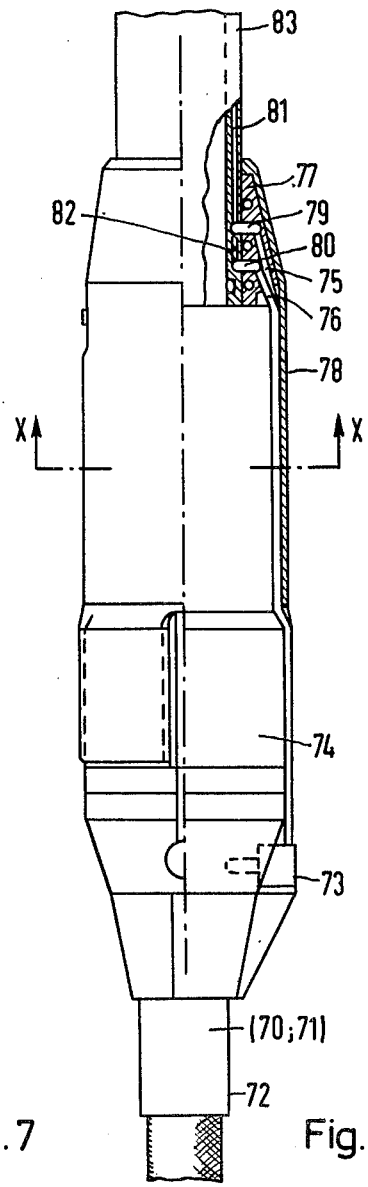
FIG. 9 illustrates a further embodiment, shown partly in section, of a conduit line located in the motor housing and gripping member.
Figure 10:
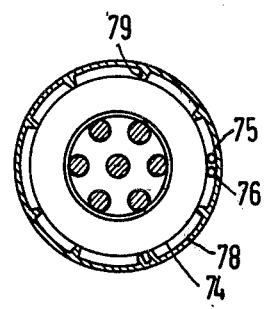
FIG. 10 is a section view taken along line X—X in FIG. 9.

FIG. 9 illustrates another embodiment of another possible cooling water and, respectively, cooling air conduit flow conveyance which lies within the scope of the invention. In this embodiment, two separate conduits 70, 71 lead from a supply hose 72 in a connector part 73 of the motor housing 74. The construction of this attachable connector part 73 may be in accordance with the embodiment shown in German Pat. 1,250,053. Leading from connector part 73 are two separate conduits 75, 76 (air and water) so as to extend along the motor handpiece until the end 77 at the hand grip. The two conduits 75 and 76 are fixedly placed on the outer annular or jacket surface of the motor housing 74 (which corresponds to the annular surface of the motor housing 20 in FIG. 2) and are encompassed by a sleeve 78. The sleeve 78 may fully encompass the conduit 75, 76 as shown in FIG. 10, or also only in the region of the two conduits. From the end part 77, which corresponds to the attachment member 14 in FIG. 2, the two conduit parts each terminate in, respectively, an annular passageway 79, 80 and from there lead through two further conduit parts 81, 82 of a grip member 83 to a head portion (not shown) of the gripping member. The admixing of the air and water into the spray, as in the embodiment of FIG. 2, is carried out directly at the drilling work tool.

From FIG. 10, which illustrates the motor housing, taken in transverse section along line X—X, it is ascertainable that the sleeve which encompasses the conduit parts 75 and 76 encompasses the entire motor handpiece at a distance which is predetermined by spacers 79.

Important advantages of the invention consist of in that the previously necessary uncoupling of the spray conduits may be omitted during removal of the gripping members, and that the spray attachment which is located externally of the handpiece is no longer required, and that the rotatability of the handpiece with reference to the motor housing is also no longer limited, as had been the case in externally located spray conduits employed in known constructions.

As may be ascertained from the exemplary embodiments, there thus becomes possible a mixing of air and the water directly at the head end of the gripping part, as well as prior thereto, for example, in the attaching portion of the motor housing. The mixing of air and water in the attaching portion of the motor housing has the advantage that only one conduit need be positioned along the motor and the gripping member. Consequently, the rotary coupling between the motor housing and handpiece may be simplified still further.

While there has been shown what is considered to be the preferred embodiment of the invention, it will be obvious that modifications may be made which come within the scope of the disclosure of the specification.

What is claimed is:

1. In a dental handpiece including an electrical motor; an essentially cylindrical housing for receiving said motor; a supply hose containing an energy supply conduit for said motor; at least one cooling media supply conduit; connector means for attaching said supply hose to one end of said housing; a rotatable drive shaft projecting from the other end of said housing; a gripping member for the handpiece, exchangeably and detachably mounted to said housing and having a power-transmission shaft engaging with said drive shaft; a head portion having a work tool provided at the end of said gripping member remote from said housing and coupled to said power shaft; said cooling media supply conduit leading from said connector means to said head portion; the improvement comprising: said cooling media supply conduit being divided into at least two fixedly displaced conduit sections respectively extending along said housing and said gripping member; and coupling means positioned concentrically to said drive shaft for interconnecting said conduit sections intermediate said housing and said gripping member; said gripping member being rotatably arranged with respect to the portion of said housing holding said drive shaft.

2. The dental handpiece as claimed in claim 1, wherein said coupling means interconnects said conduit sections when said gripping is attached to said housing.

3. The dental handpiece as claimed in claim 1, wherein said housing has a jacket portion; said cooling media conduit section for the cooling media, along said housing, being located between said jacket portion and stationary parts of said motor.

4. The dental handpiece as claimed in claim 3, wherein said conduit sections are located between said housing and the stator of said motor.

5. The dental handpiece as claimed in claim 3, wherein said conduit section for the cooling media extends along said housing, being located externally of said jacket portion; and sleeve means encompassing at least a peripheral portion of said conduit section, that is covered by said supply hose.

6. The dental handpiece as claimed in claim 5, wherein said sleeve means fully encompasses said jacket portion of the housing.

7. The dental handpiece as claimed in claim 6, wherein said sleeve means is located eccentrically relative to said motor housing.

8. The dental handpiece as claimed in claim 1, wherein said gripping member includes a grip housing, said conduit section for the cooling media, that extends along said gripping member, being located within the cross-section of said grip housing.

9. The dental handpiece as claimed in claim 1, wherein said mixing chamber is a portion of a cooling media quantity dosing valve located between said connector means and said housing.

10. The dental handpiece as claimed in claim 1, further comprising an attachment member on the end of said housing proximate said gripping member, said attachment member including a mechanical coupling element for locking said motor housing to said gripping element, and said coupling means for said conduit sections being located in said attachment member.

11. In a dental handpiece including an electrical motor; an essentially cylindrical housing for receiving said motor; a supply hose containing an energy supply conduit for said motor; at least one cooling media supply conduit; connector means for attaching said supply hose to one end of said housing; a rotatable drive shaft projecting from the other end of said housing; a gripping member for the handpiece, exchangeably and detachably mounted to said housing and having a power-transmission shaft engaging with said drive shaft; a head portion having a work tool provided at the end of said gripping member remote from said housing and coupled to said power shaft; said cooling media supply conduit leading from said connector means to said head portion; the improvement comprising: said cooling media supply conduit being divided into at least two fixedly displaced conduit sections respectively extending along said housing and said gripping member; and coupling means positioned concentrically to said drive shaft for interconnecting said conduit sections intermediate said housing and said gripping member; said cooling media supply conduits including a water and an air supply conduit; a valve positioned intermediate said connector means for said supply hose and said gripping member for dosing the infeed of water, said conduit sections being for the separate conveyance of water and air, said conduit sections terminating into separate annular spaces and into recesses at the connecting location between said housing and said gripping member so as to jointly form said coupling means, and being connected to said housing when said gripping member is attached thereto.

12. In a dental handpiece including an electrical motor; an essentially cylindrical housing for receiving said motor; a supply hose containing an energy supply conduit for said motor; at least one cooling media supply conduit; connector means for attaching said supply hose to one end of said housing; a rotatable drive shaft projecting from the other end of said housing; a gripping member for the handpiece, exchangeably and detachably mounted to said housing and having a power-transmission shaft engaging with said drive shaft; a head portion having a work tool provided at the end of said gripping member remote from said housing and coupled to said power shaft; said cooling media supply conduit leading from said connector means to said head portion; the improvement comprising: said cooling media supply conduit being divided into at least two fixedly displaced conduit sections respectively extending along said housing and said gripper member; and coupling means positioned concentrically to said drive shaft for interconnecting said conduit sections intermediate said housing and said gripping member; said cooling media supply conduit including a water supply conduit and an air supply conduit located in said supply hose; a mixing chamber communicating with the outlet ends of said water and air conduits for forming a water-air mixture; a common conduit portion leading from said mixing chamber to said head portion, said mixing chamber being located between said supply hose and said motor housing; a common conduit part for said conduit section, that extends along said housing, being connected to said mixing chamber; and second coupling means formed of an annular groove and complementary recess being connected with a conduit, common to both cooling media, of said conduit section that extends along said gripping member.

13. In a dental handpiece including an elecrical motor; an essentially cylindrical housing for receiving said motor; a supply hose containing an energy supply conduit for said motor; at least one cooling media supply conduit; connector means for attaching said supply hose to one end of said housing; a rotatable drive shaft projecting from the other end of said housing; a gripping member for the handpiece, exchangeably and detachably mounted to said housing and having a power-transmission shaft engaging with said drive shaft; a head portion having a work tool provided at the end of said gripping member remote from said housing and coupled to said power shaft; said cooling media supply conduit leading from said connector means to said head portion; the improvement comprising: said cooling media supply conduit being divided into at least two fixedly displaced conduit sections respectively extending along said housing and said gripping member; and coupling means positioned concentrically to said drive shaft for interconnecting said conduit sections intermediate said housing and said gripping member; said mixing chamber being a portion of a cooling media quantity dosing valve located between said connector means and said housing, said two cooling media supply conduits lead from said supply hose directly into said mixing chamber.

* * * * *